United States Patent [19]
Real et al.

[11] Patent Number: 5,436,347
[45] Date of Patent: Jul. 25, 1995

[54] BENZALDEHYDE INTERMEDIATES USEFUL IN THE PREPARATION OF 7-OXABICYCLOHEPTANE CARBOXYLIC ACID PROSTAGLANDIN ANALOG ANTI-THROMBOTIC AND ANTI-VASOSPASTIC COMPOUNDS AND METHOD FOR PREPARING SAME

[75] Inventors: Sharon D. Real, Pennington, N.J.; David R. Kronenthal, Yardley, Pa.

[73] Assignee: Bristol-Myers Squibb Company, Princeton, N.J.

[21] Appl. No.: 247,825

[22] Filed: May 20, 1994

Related U.S. Application Data

[62] Division of Ser. No. 67,885, May 27, 1993, Pat. No. 5,332,840.

[51] Int. Cl.⁶ .............................................. C07D 493/08
[52] U.S. Cl. ...................................... 548/215; 548/236
[58] Field of Search ........................................... 548/215

[56] References Cited

U.S. PATENT DOCUMENTS 3,974,173  8/1976  Kelly ..................................... 548/215
5,100,889  3/1992  Misra et al. ......................... 548/236

OTHER PUBLICATIONS

Agami, C. et al "Kinetic Control of Asymmetric Induction During Oxazolidine Formation from (−) -Ephedrine and Aromatic Aldehydes", Tetrahedron vol. 41, No. 3, pp. 537–540, (1985).
Takahashi, H. et al "A New Asymmetric Synthesis of (R)- and (S)-3-Arylphthalides: Extremely High Diastereoselective Reaction of Arylcarbaldehydes with Chiral [2-(1,3-Oxazolidin-2-yl)phenyl]titanium Ate Complexes", Synthesis pp. 681–682, Jul. 1992.

Primary Examiner—Donald G. Daus
Attorney, Agent, or Firm—Burton Rodney

[57] ABSTRACT

A method is provided for preparing a chiral benzaldehyde of the structure

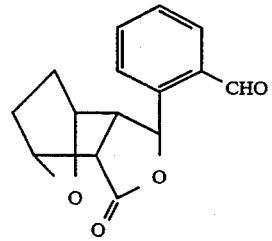

by acylating an anhydride of the structure

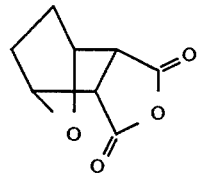

with a chiral oxazolidine of the structure

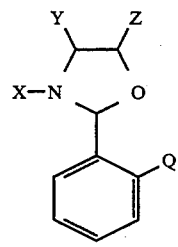

where Q is MgHal or Li, and X, Y and Z are as described herein, to form a keto acid which is reduced and cyclized. The resulting benzaldehyde may be used in making the final anti-thrombotic—anti-vasospastic compounds. Novel intermediates are also provided.

6 Claims, No Drawings

BENZALDEHYDE INTERMEDIATES USEFUL IN THE PREPARATION OF 7-OXABICYCLOHEPTANE CARBOXYLIC ACID PROSTAGLANDIN ANALOG ANTI-THROMBOTIC AND ANTI-VASOSPASTIC COMPOUNDS AND METHOD FOR PREPARING SAME

This is a division of application Ser. No. 67,885, filed May 27, 1993 now U.S. Pat. No. 5,332,840.

FIELD OF THE INVENTION

The present invention relates to benzaldehyde intermediates which may be used to prepare 7-oxabicycloheptane carboxylic acid prostaglandin analog antithrombotic—anti-vasospastic products, and to methods for preparing same.

BACKGROUND OF THE INVENTION

U.S. Pat. No. 5,100,889 to Misra et al discloses 7-oxabicycloheptyl substituted heterocyclic amide prostaglandin analogs which are thromboxane $A_2$ ($TXA_2$) receptor antagonists or combined thromboxane $A_2$ receptor antagonist/thromboxane synthetase inhibitors useful, for example, in the treatment of thrombotic and/or vasospastic diseases, and have good duration of action. Examples of compounds disclosed in Misra et al have the structural formula I

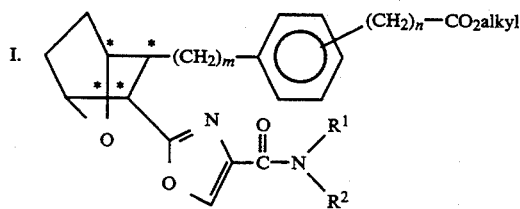

and including all stereoisomers thereof, wherein
m is 1, 2 or 3; n is 0, 1, 2, 3 or 4;
$R^1$ is hydrogen, lower alkyl, aralkyl, aryl, cycloalkyl, cycloalkylalkyl, or amide

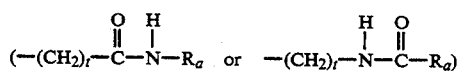

wherein t is 1 to 12 and $R_a$ is lower alkyl, aryl, cycloalkyl, or cycloalkylalkyl);
$R^2$ is hydrogen, lower alkyl, aryl, or aralkyl; or $R^1$ and $R^2$ together with the nitrogen to which they are linked may form a 5- to 8- membered ring.

Misra et al disclose that these compounds may be prepared by transmetallating bromophenylalkyl B

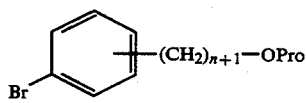

by treatment with $t$-$C_4H_9Li$ or $n$-$C_4H_9Li$ or subjecting B to a Grignard reaction by treatment with Mg, and then condensing with benzopyran-3-ol or benzofuran-1-ol C

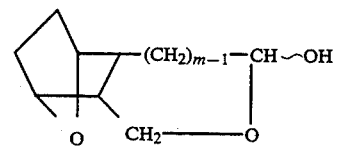

to form the condensed 7-oxabicycloheptane alcohol compound of the structure Z

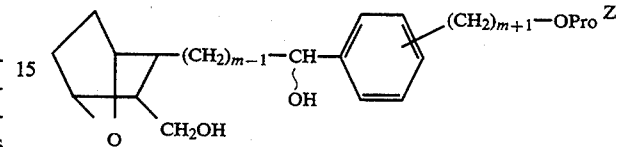

and then subjecting the condensed compound to hydrogenolysis to form the following alcohol:

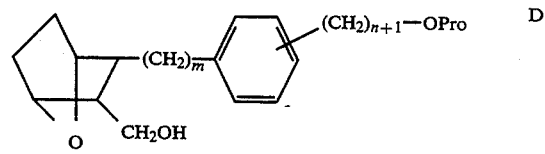

Where Pro is thexyldimethylsilyl or t-butyldimethylsilyl, the alcohol is acetylated and the silyl protecting group of the so-formed acetate is removed to form the following acetate:

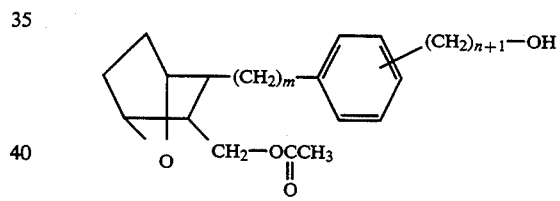

which is treated with a protecting compound and the acetate is removed by treatment with aqueous hydroxide or excess methyllithium to form the followng alcohol:

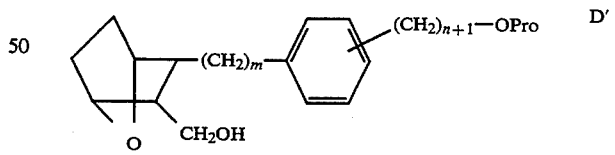

(where Pro is t-butyldiphenylsilyl). The protected alcohol is subjected to a Jones oxidation to form the following acid:

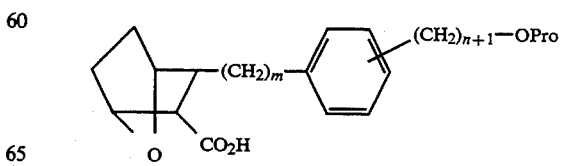

The so-formed carboxylic acid intermediate is then employed to make the final compound.

In a more preferred procedure, Misra et al disclose protecting the alcohol function of alcohol Z to form the protected alcohol

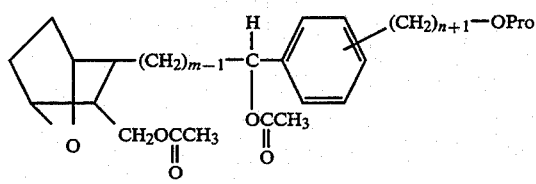

subjecting the protected alcohol to a Jones oxidation and esterification to form the ester

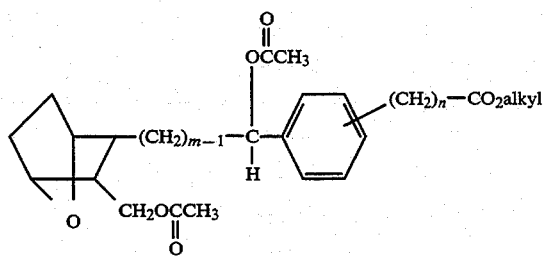

which is made to undergo hydrogenolysis and subsequent removal of the acetate protecting group by transesterification to afford the alcohol

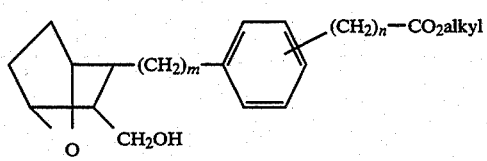

which is subjected to a Jones oxidation to form the carboxylic acid intermediate II

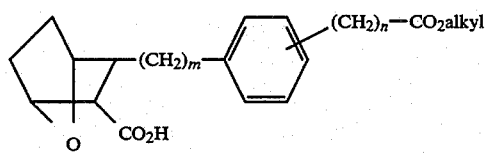

In an alternative procedure where n is 1, the above carboxylic acid intermediate II is formed by treating D' with acetic anhydride and removing the protecting group to form the acetate alcohol

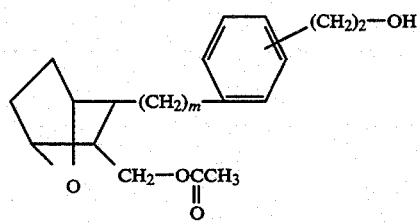

which is made to undergo a Dess-Martin oxidation to form the aldehyde

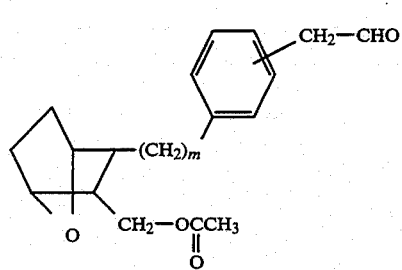

The above aldehyde is oxidized and esterified to the corresponding acetate ester, deprotected, and subjected to a Jones oxidation to form carboxylic acid II where n is 1.

DESCRIPTION OF THE INVENTION

In accordance with the present invention, methods are provided for preparing chiral intermediates for use in the preparation of 7-oxabicycloheptyl substituted oxazole amide prostaglandin analogs as described hereinafter which are useful as anti-thrombotic and antivasospastic compounds.

The methods of the invention are outlined in Reaction Schemes I to VI set out hereinafter.

Reaction Scheme I - Preparation of Benzaldehyde Intermediate IIIA

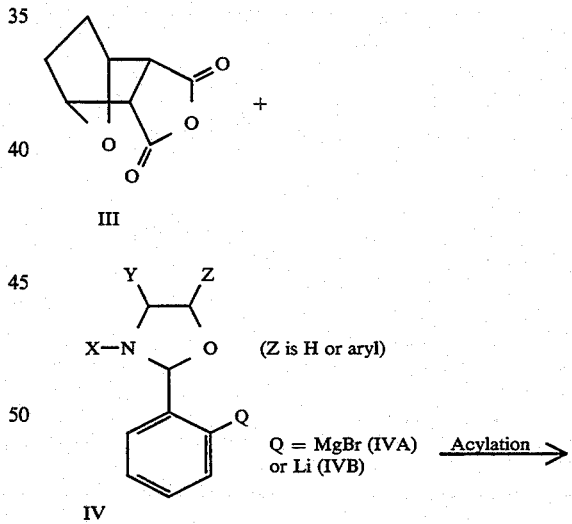

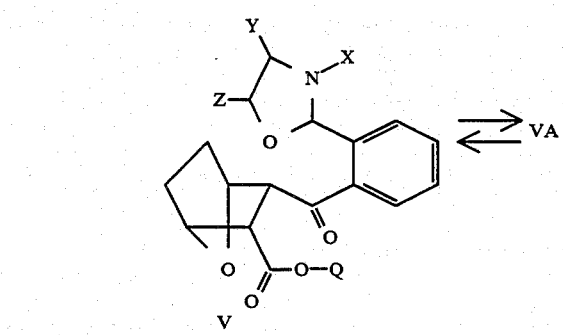

5,436,347
-continued
Reaction Scheme I - Preparation of Benzaldehyde Intermediate IIIA
-continued
Reaction Scheme II - Preparation of Starting Oxazolidine IV
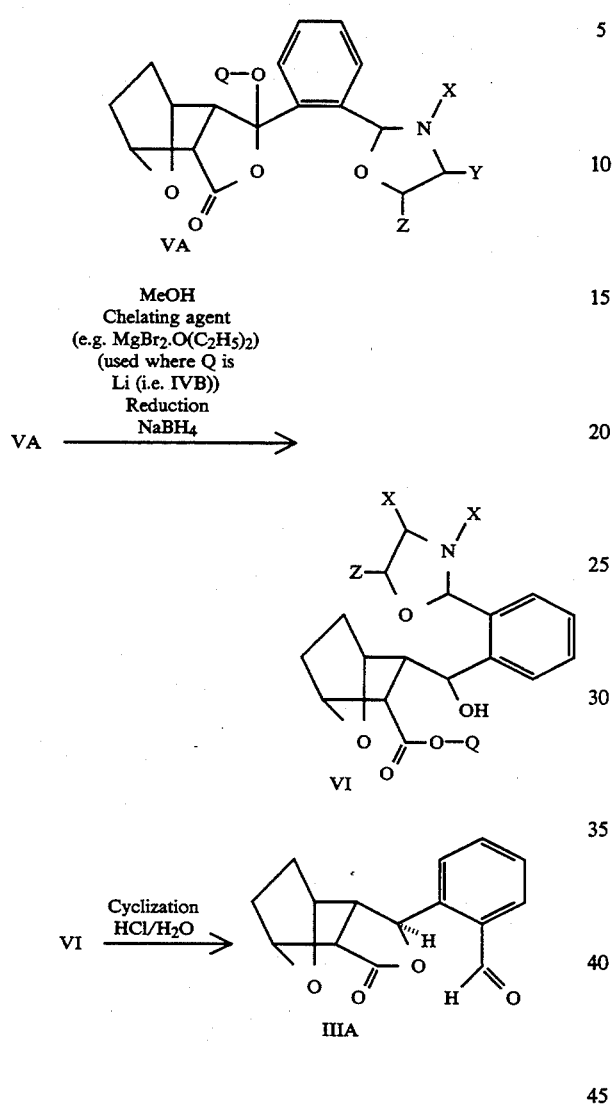
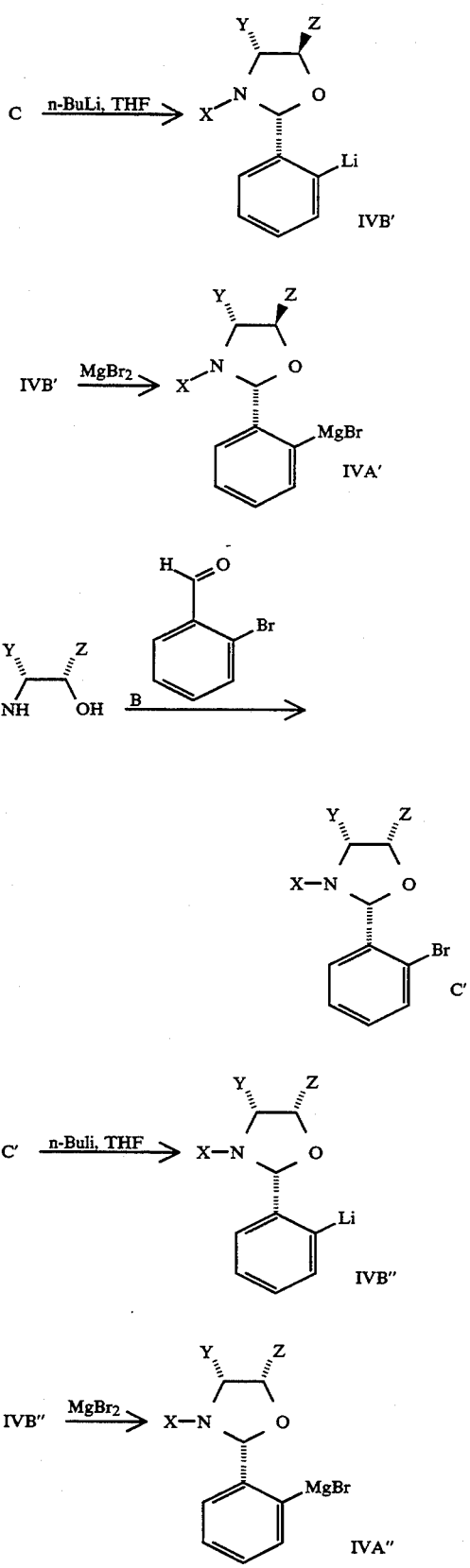

5,436,347
-continued
Reaction Scheme II - Preparation of Starting Oxazolidine IV
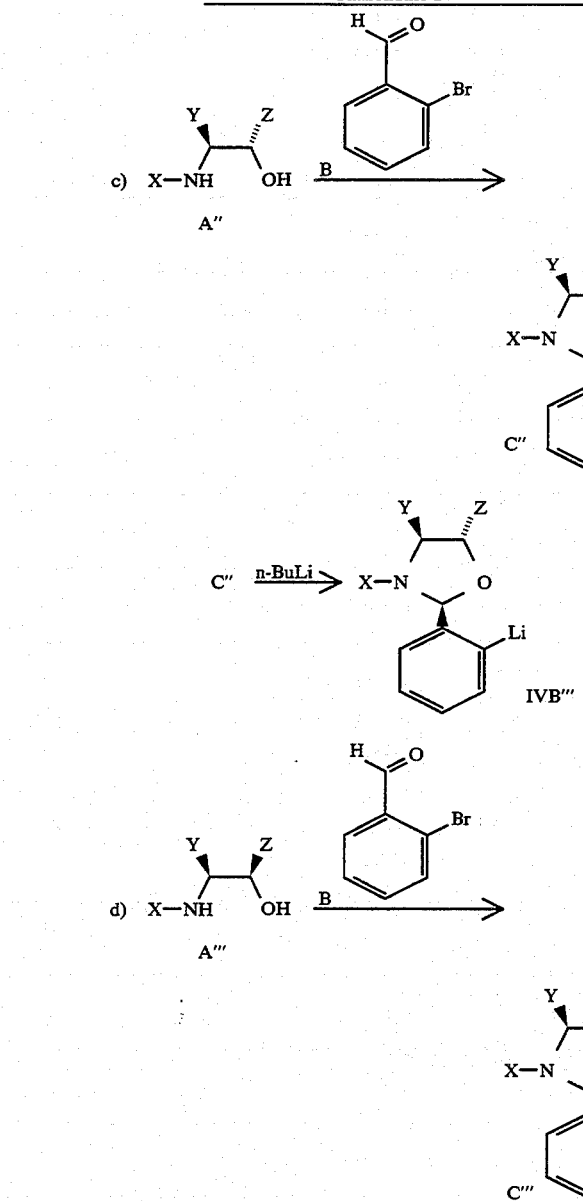
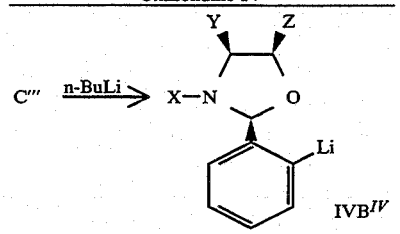
Reaction Scheme III - Preparation of Carboxylic Acid Intermediate IIA
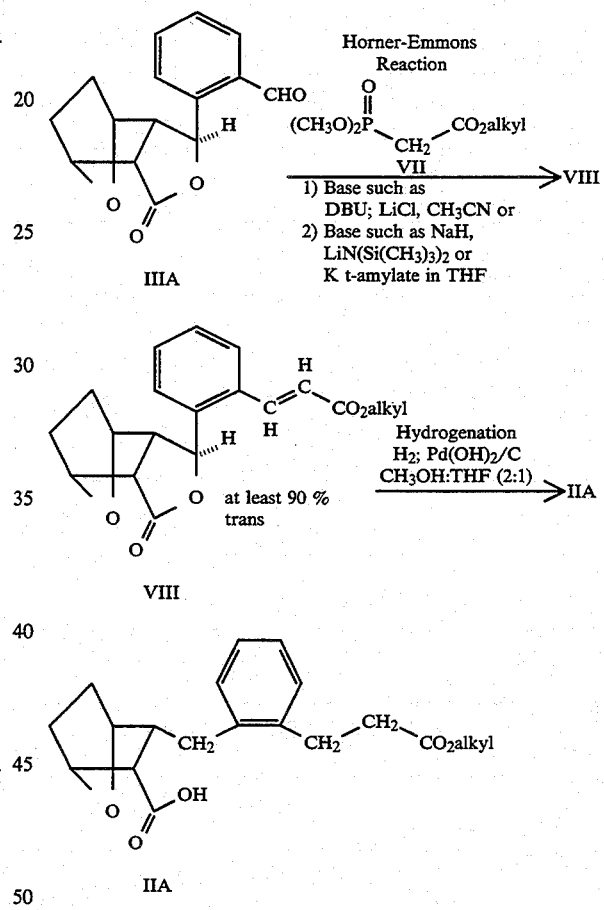
Reaction Scheme IV - Alternate Preparation of Carboxylic Acid Intermediate IIA
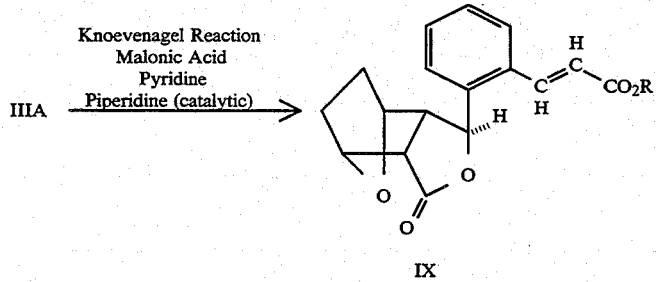

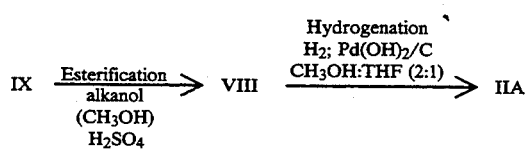
Reaction Scheme V - Preparation of Final Product
Starting with Carboxylic Acid Intermediate IIA
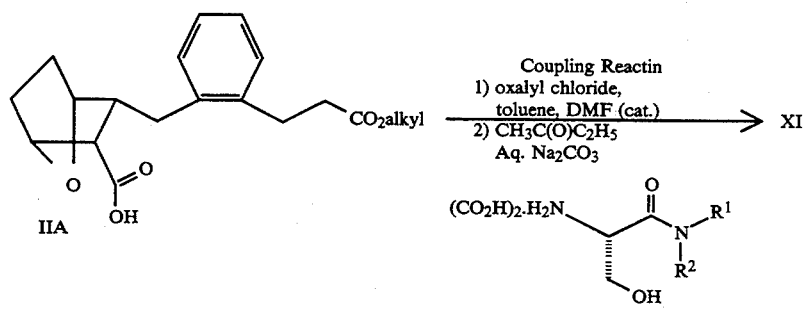
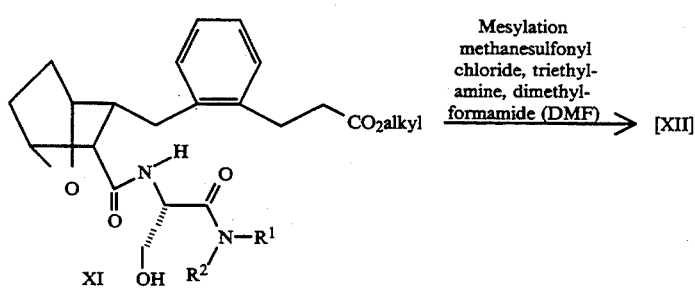
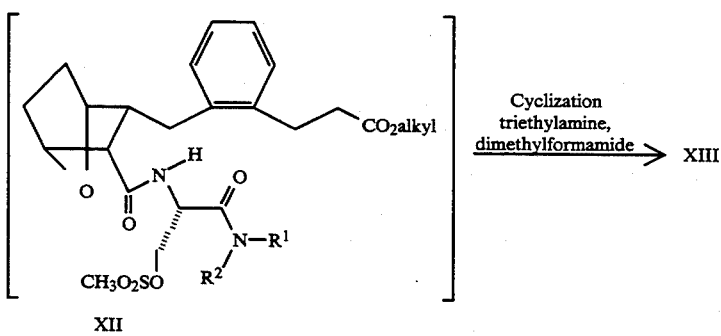
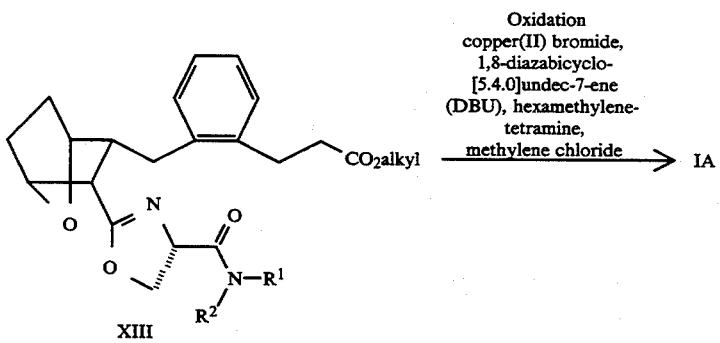

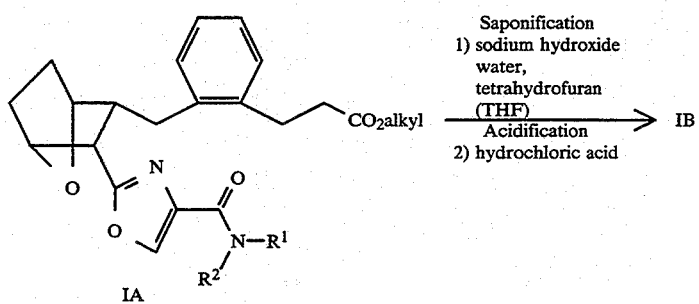
IA
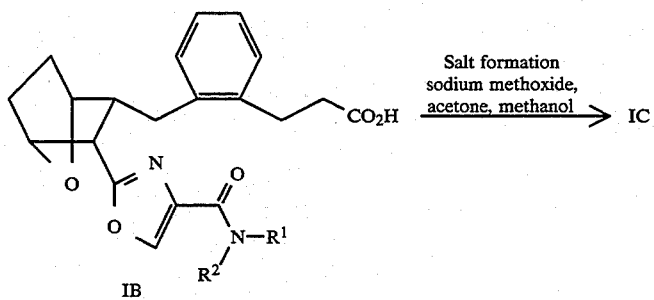
IB
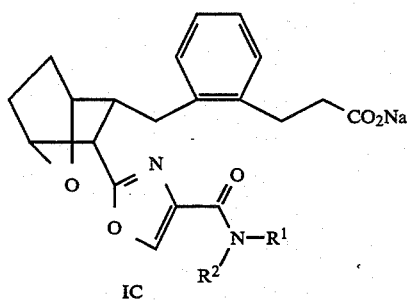
IC
Reaction Scheme VI - Preparation of Starting Compound X
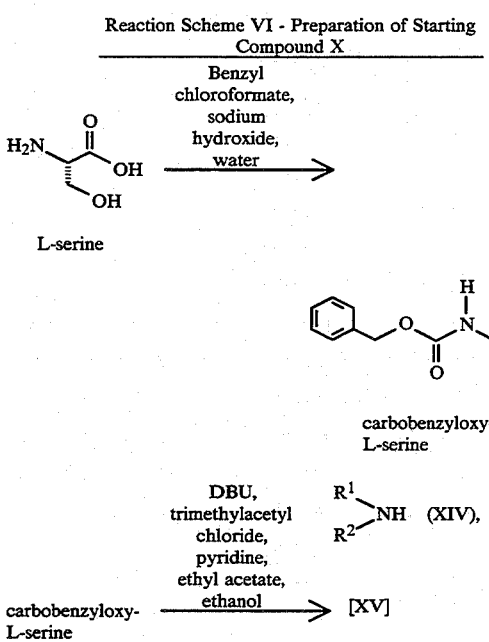
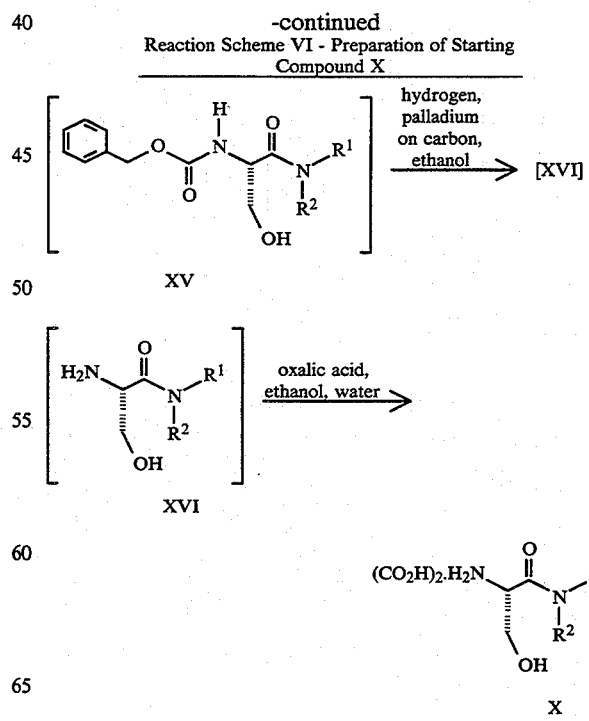

Referring to Reaction Scheme I, in accordance with the method of the invention, chiral benzaldehyde intermediate IIIA is prepared starting with anhydride III which is used to acylate IV

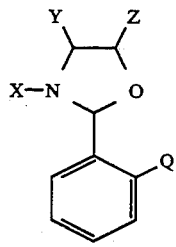

IV wherein X is lower alkyl or aralkyl, preferably methyl;
Y is lower alkyl, aryl or aralkyl, preferably methyl;
Z is aryl or H, preferably phenyl; and
Q is MgBr or Li.

Where in IV, Z is aryl, novel intermediates are provided having the structure IVa

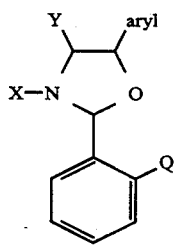

IVa wherein X, Y and Q are as defined above.

In one aspect of the present invention, the above referred to reaction of anhydride III with IV is carried out by subjecting anhydride III to a Grignard reaction with Grignard reagent IV wherein Q is MgBr (IVA) as follows. A cooled mixture of anhydride III in an inert organic solvent such as THF, toluene, diethyl ether, methyl t-butyl ether, or mixtures of two or more thereof, is mixed with a Grignard reagent IVA

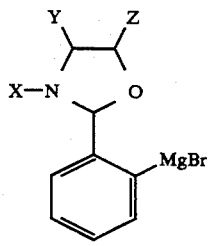

IVA which preferably is the isomer

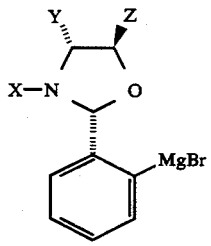

IVA' or

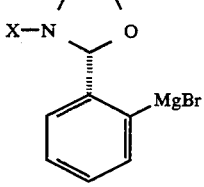

IVA"

wherein Z is phenyl, Y is methyl and X is methyl (prepared as described hereinafter with respect to Reaction Scheme II) to form keto acid salt V (which is a novel compound in accordance with the present invention) and is in equilibrium with VA, as shown.

After cooling, the keto acid salt V is reduced by treatment of V with a reducing agent such as sodium borohydride, lithium borohydride or zinc borohydride in the presence of an alcohol solvent such as methanol or ethanol to form intermediate VI (which will be at least 90% of a single epimer) (which is a novel compound in accordance with the present invention). Intermediate VI is cyclized by treatment with a strong acid such as HCl, $H_2SO_4$, p-toluene sulfonic acid, or oxalic acid to form benzaldehyde IIIA which is predominantly (that is at least 90%) epimer A

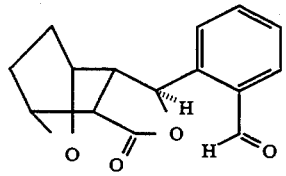

epimer A

The ratio of desired to undesired enantiomers of aldehyde IIIA obtained using the above conditions will range from about 80:20 to about 99.5:0.5. Where the Grignard reagent IVA" is employed, the desired enantiomer to undesired enantiomer will be obtained in a ratio of from about 95:5 to about 99.5:0.5.

When in oxazolidine IV, Q is Li (IVB), the acylation step is carried out by treating a cooled mixture of anhydride III in an inert organic solvent such as THF, toluene, diethyl ether, methyl t-butyl ether or mixtures of two or more thereof, with a cooled solution of lithiated oxazolidine IVB

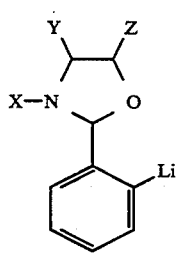

IVB which preferably is the isomer

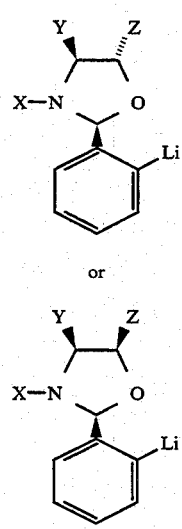

wherein Z is phenyl, Y is methyl and X is methyl, in the same solvent as anhydride III, to form keto acid salt V which is treated with a chelating agent such as MgBr·O(C₂H₅)₂, and is reduced and cyclized, as described hereinbefore, to form benzaldehyde IIIA. The chelating agent is necessary to produce predominantly (that is at least 90% of) one epimer in the reduction. Omission of the MgBr·O(C₂H₅)₂ results in the formation of both epimers either of which will be useful in forming IIA.

The ratio of desired to undesired enantiomers of aldehyde IIIA obtained using the above conditions will range from about 60:40 to about 70:30.

Referring to Reaction Scheme II, the various isomers of oxazolidine IV may be prepared as follows.

In sequence IIa) aminoalcohol A, which preferably is (−)-pseudoephedrine

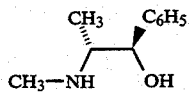

is condensed with 2-bromobenzaldehyde B in the presence of a solvent such as toluene, EtOH, CH₂Cl₂ or THF, to form the oxazolidine C. A mixture of oxazolidine C in an inert organic solvent such as THF, toluene, diethyl ether, methyl t-butyl ether or mixtures thereof under an inert atmosphere such as argon or nitrogen, is treated with an alkylated lithium such as n-butyllithium, t-butyl lithium or lithium metal, to form the lithiated oxazolidine IVB′

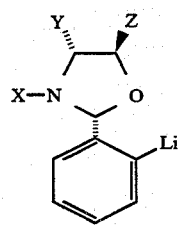

which is added to a cooled slurry of magnesium bromide to form the Grignard reagent IVA′.

Alternatively as seen in Reaction Scheme IIb), the starting aminoalcohol A′ which preferably is (+)-ephedrine

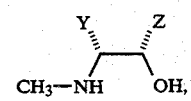

may be employed in place of (−)-pseudoephedrine to form Grignard reagent IVA″.

Reaction Schemes IIc) and d) depict reaction sequences for preparing IVB‴ and IVB^{IV} starting with aminoalcohols A″ and A‴, respectively. The reactions are essentially as described with respect to Reaction Scheme IIa) except that the lithiated oxazolidine IVB‴ and IVB^{IV} are not reacted with MgBr₂ and are used in the lithiated form.

The novel intermediates which are part of the present invention have the structures

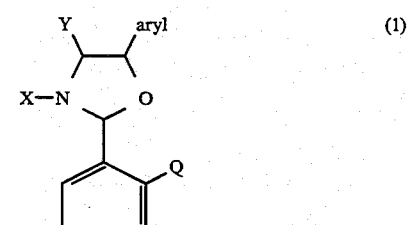

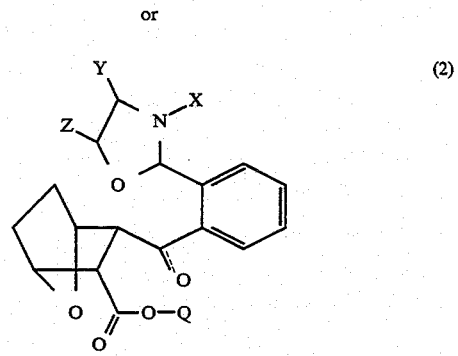

including stereoisomers of structures (1) and (2) wherein in structure (1) Q is MgHal (where Hal is Br, Cl or I) or Li;

X is lower alkyl or aralkyl;

Y is lower alkyl, aryl or aralkyl;

Z is aryl or H;

with the provisos where structure (2) is V, then V will be in equilibrium with VA; and wherein in structure (2) X, Y and Z can be as defined in structure (1) and =====o represents —OH or =O and includes all stereoisomers.

In preferred embodiments, in structures (1) and (2) Y is CH₃, Z is C₆H₅, and X is CH₃.

Preferred isomers of formula (1) compounds have the structures

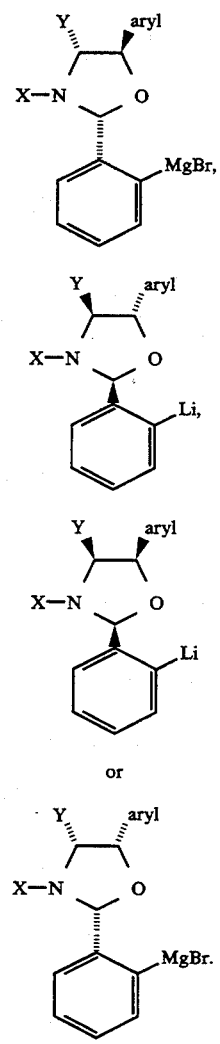
(a)
(b)
(c)
or
(d)
More preferred intermediates of formula (1) have the structure
 (1a)
or
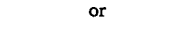 (1b)
 (1c)
or
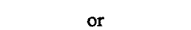 (1d)
wherein in (1a) Q is Li, in (1b) Q is MgBr, in (1c) Q is Li and in (1d) Q is MgBr.
Compounds of formula (2) will preferably include
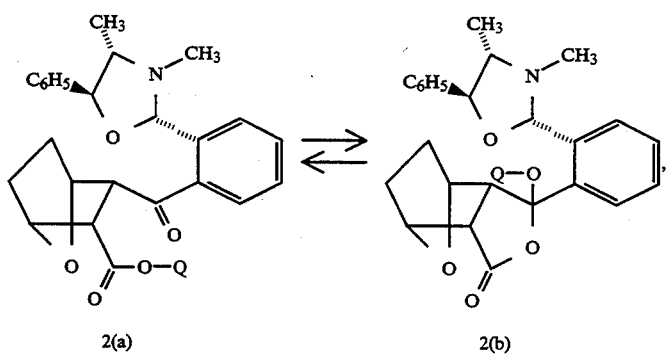
2(a)  2(b)

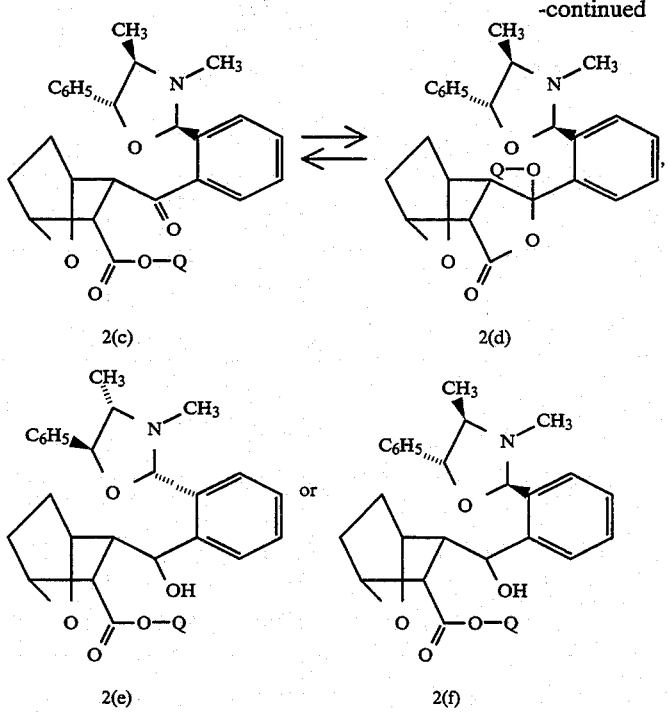

2(c)

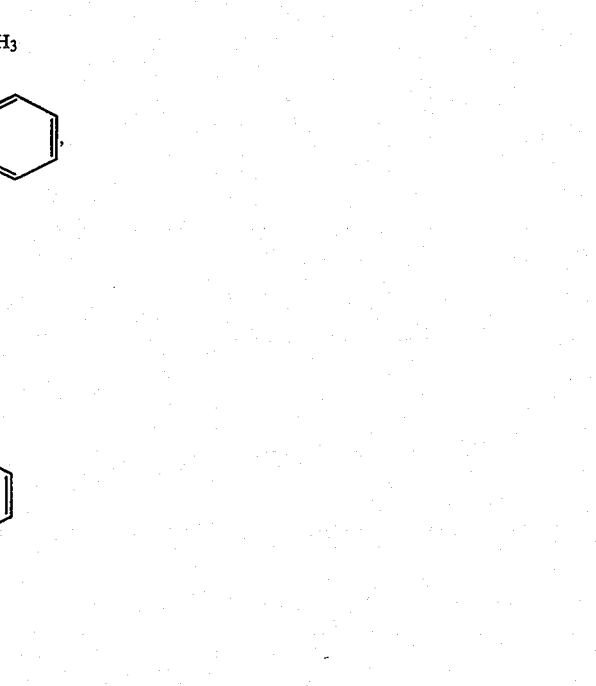

2(d)

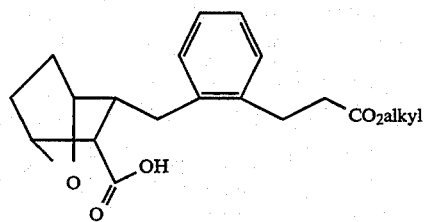

2(e)    or    2(f)

In all of the above formulae, including in preferred compounds, where the stereochemistry is not specified, it is intended that all stereoisomers are to be included.

DETAILED DESCRIPTION OF INVENTION

Referring to Reaction Scheme I, the benzaldehyde intermediate IIIA is prepared by reacting anhydride III with IV employing a molar ratio of IV:III of within the range of from about 0.5:1 to about 5:1, preferably from about 1:1 to about 1.4:1, at a temperature within the range of from about −80° to about 25° C., preferably from about −70° to about −10° C., to form keto acid salt V.

Reduction of keto acid salt V is carried out employing a molar ratio of reducing agent:keto acid salt V of within the range of from about 2:1 to about 1:1, preferably from about 1.5:1 to about 1.2:1, to form salt compound VI.

The salt VI is cyclized employing a molar ratio of acid:salt VI of within the range of from about 100:1 to about 4:1, preferably from about 5.5:1 to about 4.5:1.

Referring to Reaction Scheme II, the 2-bromobenzaldehyde B will be employed in a molar ratio to the aminoalcohol A, A', A" or A'" of within the range of from about 0.5:1 to about 1.5:1, preferably from about 1.1:1 to about 0.9:1. The reaction will be carried out at a temperature within the range of from about 40° to about 150° C., preferably from about 100° to about 110° C., to form the oxazolidine derivative C, C', C" or C'", resp.

The oxazolidine derivative C, C', C" or C'" is lithiated employing a molar ratio of alkylated lithium compound: oxazolidine derivative of within the range of from about 1.2:1 to about 0.9:1, preferably from about 1.1:1 to about 1:1. The lithiation is carried out at a temperature within the range of from about −78° to about 0° C., preferably from about −70° to about −50° C.

Where it is desired to form the Grignard reagent IVA' or IVA", the lithiated oxazolidine derivative will be treated with MgBr$_2$ employing a molar ratio of MgBr$_2$:lithiated compound of within the range of from about 1:1 to about 10:1, preferably from about 1.1:1 to about 1.2:1, at a temperature within the range of from about −80° to about 0° C., preferably from about −30° to about −5° C.

As seen in Reaction Scheme III, the benzaldehyde IIIA is used in preparing carboxylic acid starting material IIA IIA

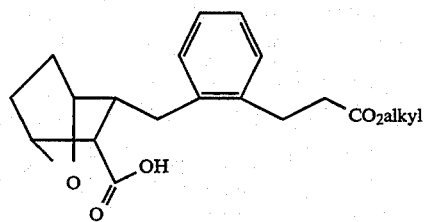

As shown in Reaction Scheme III, carboxylic acid IIA is prepared from starting benzaldehyde IIIA, which is preferably in chiral or substantially enantiomerically pure form, which is made to undergo a Horner-Emmons reaction wherein aldehyde IIIA is treated with a phosphonic diester compound VII in the presence of a base such as 1,8-diazabicyclo[5.4.0]-undec-7-ene (DBU), 1,5-diazabicyclo[4.3.0]non-5-ene (DBN), or diisopropylethylamine, preferably DBU, and an inert organic solvent such as acetonitrile, THF, dimethoxyethane or toluene, preferably, acetonitrile, and preferably an alkali metal salt such as lithium chloride, to form the ester VIII wherein alkyl can be, for example, methyl or ethyl. As shown in Scheme III, the ester VIII will be primarily in the form of the trans isomer.

Alternatively, the Horner-Emmons reaction may be carried out by substituting for DBU as a base, an alkali metal hydride such as sodium hydride, lithium bis(trimethylsilylamide, or Kt-amylate in an inert organic solvent such as THF, toluene or dimethoxyethane.

In another variation on Scheme III, the aldehyde IIIA may be homologated to form ester VIII by treating IIIA with a magnesium salt of a monoalkyl malonate of the structure IVA

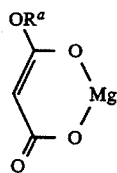

wherein $R^a$ is a lower alkyl, such as methyl or ethyl, in the presence of THF or other etheral solvent such as diethyl ether.

The ester VIII (primarily in the form of the trans isomer) will be subjected to a hydrogenation wherein ester VIII is treated with hydrogen in the presence of a hydrogenation catalyst such as $Pd(OH)_2/C$, or Pd/C, and in the presence of an alcohol solvent such as methanol or ethanol, and an inert organic solvent such as THF, ethyl acetate or dioxane, to form carboxylic acid IIA.

The Horner-Emmons reaction is carried out in the presence of base and optionally an alkali metal salt such as a lithium halide, for example, lithium chloride, lithium bromide or lithium iodide, employing a molar ratio of phosphonic acid VII: aldehyde IIIA of within the range of from about 1:1 to about 1.2:1, preferably from about 1.05:1 to about 1:1, under an inert atmosphere such as argon or nitrogen, to form the ester VIII in a ratio of trans:cis isomers of within the range of from about 14:1 to about 36:1.

Where ester VIII is formed by homologation of aldehyde IIIA employing the magnesium salt of a monoalkylmalonate (IVA), the magnesium salt will be employed in a molar ratio to aldehyde IIIA of within the range of from about 1:1 to about 2:1.

In an alternative embodiment as shown in Reaction Scheme IV, carboxylic acid intermediate IIA is formed by subjecting benzyaldehyde IIIA to a Knoevenagel reaction where IIIA is treated with malonic acid in the presence of base-solvent such as pyridine, 2,6-lutidine or collidine, and a catalytic amount of piperidine, to form acid IX. Acid IX may then be esterified, for example, by reaction with an alkanol, such as methanol or ethanol, in the presence of a strong acid catalyst such as sulfuric acid, p-toluenesulfonic acid or camphorsulfonic acid, to form the ester VIII. Ester VIII may then be hydrogenaced as described above with respect to Reaction Sequence IV, to form carboxylic acid intermediate IIA.

The Knoevenagel reaction is carried out employing a molar ratio of malonic acid:aldehyde IIIA of within the range of from about 6:1 to about 3:1, preferably from about 5:1 to about 4.5:1. The reaction is carried out at a temperature within the range of from about 80° to about 85° C. The resulting acid IX is esterified with an alkanol, preferably methanol or ethanol, employing conventional techniques to form the ester VIII which may be hydrogenated as described above to form carboxylic acid IIA.

As seen in Reaction Scheme V, the carboxylic acid IIA intermediate is employed to prepare a thromboxane receptor antagonist IA-IC. As seen in Scheme V, carboxylic acid IIA is subjected to a coupling reaction wherein carboxylic acid IIA in an inert solvent such as toluene, dichloromethane, or dichloroethane is treated under an inert atmosphere with a catalytic amount of DMF. The resulting mixture is cooled below 0° C. and oxalyl chloride or other reagent for acid chloride formation such as thionyl chloride is added to form an acid chloride solution. When thionyl chloride is to be employed, carboxylic acid IIA need not be treated with catalytic DMF.

Amide X (prepared as described in Scheme VI) is added to aqueous sodium bicarbonate solution and an inert organic solvent such as methyl ethyl ketone, dichloromethane or THF is added to form a biphasic mixture which is cooled to from about 30° to about −10° C. The previously prepared acid chloride solution is added and the mixture heated to a temperature within the range of from about 40° to about 80° C. to form amide XI.

Amide XI is mesylated by treating a solution of amide XI in DMF or other solvent such as dichloromethane, ethyl acetate or THF, with a weak organic base such as triethylamine, pyridine or 2,6-lutidine and then while maintaining the mixture below about 5° C., methanesulfonyl chloride is added to form the mesylate XII. Mesylate XII is cyclized by treating XI with triethylamine or other weak organic base as set out above, in the presence of DMF or other solvent as set out above to form oxazoline XIII.

Oxazoline XIII is oxidized using cupric bromide and 1,8-diazabicyclo[5.4.0]undec-7-ene (DBU) in the presence of hexamethylenetetramine and inert organic solvent such as methylene chloride to form oxazole ester IA which is saponified by treatment with strong base such as NaOH, KOH and the like, in aqueous-organic solvent such as THF or dioxane, and then is acidified by treatment with strong acid such as HCl, $H_2SO_4$ or trifluoroacetic acid to form oxazole acid IB. Oxazole acid IB may then be treated with alkali metal alkoxide such as sodium methoxide, sodium 2-ethyl-hexanoate or sodium ethoxide, in the presence of inert organic solvent such as acetone, THF or ethyl acetate, and an alcohol such as methanol or ethanol to form oxazole salt IC.

Referring to Reaction Scheme VI, the amide x (used in Scheme V) is prepared by reacting an aqueous solution of L-serine and NaOH with benzyl chloroformate to form carbobenzyloxy-L-serine which is treated with DBU under an inert atmosphere. Thereafter trimethylacetyl chloride and amine XIV are added to form amide XV which is deprotected by treatment with $H_2$ and Pd/C in the presence of an alcohol solvent, such as ethanol or methanol, to form amide XVI which is treated with oxalic acid or another acid such as HCl or trifluoroacetic acid in the presence of alcohol solvent such as ethanol or methanol to form amide x.

In the amine XIV, $R^1$ and $R^2$ are as defined in U.S. Pat. No. 5,100,889 which is incorporated herein by reference.

Thus, $R^1$ is hydrogen, lower alkyl, aralkyl, aryl, cycloalkyl, cycloalkylalkyl, or amide

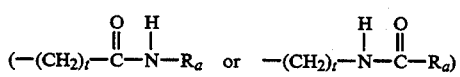

wherein t is 1 to 12 and $R_a$ is lower alkyl, aryl, cycloalkyl, or cycloalkylalkyl); and $R^2$ is hydrogen, lower alkyl, aryl, or aralkyl; or $R^1$ and $R^2$ together with the nitrogen to which they are linked may form a 5- to 8- membered ring.

R[1] is preferably lower alkyl such as n-pentyl, aryl such as phenyl, halophenyl such as 4-chlorophenyl, or cyclohexylalkyl, such as cyclohexylbutyl.

R[2] is preferably H or phenyl.

In carrying out the preparation of the thromboxane receptor antagonist products IB and IC, as shown in Scheme V, amide x is employed in a molar ratio to acid IIA of within the range of from about 1.5:1 to about 1:1, preferably from about 1.1:1 to about 1:1, to form amide XI. Amide XI is mesylated employing a molar ratio of methanesulfonyl chloride:XI of within the range of from about 2:1 to about 1:1, preferably from about 1.3:1 to about 1:1 and a temperature within the range of from about −20° to about 60° C., preferably from about 0° to about 25° C.

The resulting mesylate XII is cyclized employing a molar ratio of triethylamine or other organic base:XII of within the range of from about 4:1 to about 2:1, preferably from about 3.5:1 to about 2.5:1, to form oxazoline XIII. Other organic bases which may be employed include diisopropylethylamine, pyridine or 2,6-lutidine.

The cupric bromide oxidation of oxazoline XIII is carried out at a temperature of within the range of from about 20° C. to about 70° C., employing a molar ratio of cupric bromide to oxazoline XIII of within the range of from about 2:1 to about 6:1 and a molar ratio of cupric bromide to DBU of within the range of from about 1:1 to about 1:3 in an inert solvent, preferably methylene chloride. The above oxidation is preferably carried out in the presence of a base such as hexamethylenetetramine as disclosed in U.S. application Ser. No. 20,948 filed Feb. 22, 1993, which is incorporated herein by reference.

The so-formed oxazole ester IA may then be hydrolyzed employing conventional techniques such as by treatment with an aqueous solution of alkali metal base and then aqueous acid to form the corresponding acid IB which may be treated with sodium methoxide, sodium 2-ethylhexanoate or sodium ethoxide to form salt IC in the presence of acetone/methanol.

The term "lower alkyl" or "alkyl" as employed herein includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 substituents such as halo, alkenyl, alkynyl, aryl, alkyl-aryl, haloaryl, cycloalkyl, or alkylcycloalkyl.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, and/or alkoxy groups.

The term "aryl" or "Ar" as employed herein refers to monocyclic or bicyclic aromatic groups containing from 6 to 10 carbons in the ring portion, such as phenyl or naphthyl. Aryl (or Ar), phenyl or naphthyl may include substituted aryl, substituted phenyl or substituted naphthyl, which may include 1 or 2 substituents on either the phenyl or naphthyl such as lower alkyl, trifluoromethyl, halogen (Cl, Br, I or F), alkylsulfonyl, and/or arylsulfonyl.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to Cl, Br, F or I, with Cl preferred.

The final compounds IB and IC prepared by the method of this invention are thromboxane receptor antagonists and as such are useful as inhibitors of thromboxane receptor mediated actions. The term "thromboxane receptor antagonist" includes compounds which are so-called thromboxane A$^2$ receptor antagonists, thromboxane A$^2$ antagonists, thromboxane A$^2$/prostaglandin endoperoxide antagonists, TP-receptor antagonists, or thromboxane antagonists.

The compounds prepared by the method of the invention are also thromboxane synthetase inhibitors and thus are useful as inhibitors of thromboxane production.

Examples of various utilities of the compounds prepared by the method of the invention are set out in U.S. Pat. No. 5,100,889.

The following Examples represent preferred embodiments of the present invention. Unless otherwise indicated, all temperatures are expressed in degrees Centigrade.

EXAMPLE 1

(2R,4R,5R)-2-(2-Bromophenyl)-3,4-dimethyl-5-phenyloxazolidine

A. (−)-Pseudoephedrine

In a 500-mL, 3-necked flask equipped with overhead stirrer, addition funnel and nitrogen inlet, (−)-pseudoephedrine hydrochloride (30.01 g, 149 mmole, 1.0 eq) was dissolved in 234 mL of distilled H$_2$O. With constant stirring, 2.5N NaOH (66 mL, 165 mmole, 1.1 eq) was added via the addition funnel over 5 min resulting in the formation of a white precipitate (pH of the mixture=14). The mixture was stirred in an ice bath for 3 h. The white solid was collected via vacuum filtration and washed with distilled H$_2$O (3×200 mL) until the pH of the filtrate was 10. Drying in vacuo gave 17.88 g (73%) of (−)-pseudoephedrine as a white solid.

B. (2R, 4R, 5R) -2- (2-Bromophenyl) -3,4-dimethyl-5-phenyloxazolidine

To a solution of 2-bromobenzaldehyde (18.78 g, 101.50 mmole, 1.0 eq) in toluene (100 mL) was added (−)-pseudoephedrine (16.73 g, 101.24 mmole, 1.0 eq). The mixture was refluxed for 16 h under an argon atmosphere using a Dean-Stark trap to remove the generated water. Concentration in vacuo gave 33.53 g (100%, corrected for 2 wt % toluene by $^1$H NMR) of a 40:1 mixture of title compound and a minor diastereomer as a light yellow oil.

EXAMPLE 2

[2S-(2α,3aα,4β,7β,7aα]-2-(Octahydro-3-oxo-4,7-epoxyisobenzofuran-1-yl)benzaldehye A. MaBr$_2$ To a 250-mL, 3-necked flask equipped with overhead stirrer, condenser, and argon inlet were added 1.66 g of Mg turnings (68.31 mmol, 1.3 eq), 30 mL of THF and 1,2-dibromopropane (2.90 g, 14.36 mmol, 0.27 eq). Within 5 min the mixture began to reflux. The remainder of the dibromopropane (9.64 g, 47.75 mmol, 0.91 eq) was added dropwise over 10 min to maintain a gentle reflux. The reaction was refluxed for an additional 2 h. At reflux the mixture was yellow and contained insoluble MgBr$_2$. The reaction was then cooled to room temperature. On cooling the mixture turns into a thick off-white slurry with residual Mg turnings.

B. (2R,4R,5R)-2-(3,4-Dimethyl-5-phenyloxazolidin-2-yl)phenyl lithium

In a separate flask, the oxazolidine in the form of the mixture of Example 1 (17.43 g, 52.62 mmol, 1 eq) was dissolved in 25 mL of THF under an argon atmosphere. The solution was cooled to −70° C. (internal temperature) and n-C$_4$H$_9$Li (n-BuLi) (21 mL, 52.5 mmol, 1 eq) was added dropwise over 10 min such that the internal temperature did not rise above −50° C. The reaction was brought back to −70° C., and stirred for 2 h.

C. [1R-[1α,2α,3α[2R-(2α,3β,4α,5β)],4α]]-3-[2-(3,4-Dimethyl-5-phenyl-2-oxazolidinyl)-benzoyl]-7-oxabicyclo[2.2.1]heptane-2-carboxylic acid, bromomagnesium salt The Part A MgBr$_2$ slurry was further cooled to −30° C. To this reaction mixture was added the Part B lithiated oxazolidine solution, via cannula, over 10 min such that the internal temperature of the combined solution did not rise above −30° C. The MgBr$_2$-oxazolidine mixture changes from a thick to a thin slurry. This mixture was stirred between −30° and −20° C. for 5 min and then warmed to −5° C. over 15 min. The mixture at this point is yellow with residual insoluble MgBr$_2$. After cooling to −60° C., a solution of (3aα, 4β,7β,7aα)-hexahydro-4,7-epoxyiso-benzofuran-1,3-dione (6615.93 g, 35.26 mmol, 0.67 eq) in 15 mL of THF was added dropwise to the reaction mixture over 5 min such that the internal temperature remained below −50° C. After the addition was complete, the solution was clear yellow with a few residual Mg turnings. The reaction was stirred between −55° and −45° C. for 1.25 h. The internal temperature was raised to −35° (±5)° C. and the reaction was stirred for 1.75 h. At this point the reaction mixture containing the title compound was quenched at −30° C. with 60 mL of anhydrous MeOH.

D. [2S-(2α,3aα,4β,7β,7aα)]-2-(Octahydro-3-oxo-4,7-epoxy-isobenzofuran-1-yl)benzaldehyde The Part C mixture was cooled to −60° C. and NaBH$_4$ (1.87 g, 49.36 mmol, 1.4 eq) was added in one portion. The mixture was warmed to −30° (±5)° C. and stirred for 1.25 h. The reaction was quenched at −30° C. with 10 mL of acetone and poured into 60 mL of 3N HCl at 10° C. while stirring. Stirring was continued for 14 h at room temperature. The mixture was concentrated in vacuo. EtOAc was added and the organic and aqueous layers were separated. The EtOAc layer was washed with 1N HCl. The combined aqueous layers were extracted 2× with EtOAc. The combined EtOAc layers were washed with brine, dried with MgSO$_4$ and concentrated to yield 8.7 g of a pale yellow solid. This solid was dissolved in 40 mL of THF with heating. The solution was removed from the heat and seeded. HCl (0.5N, 200 mL) was added slowly with stirring. A pale yellow solid precipitated from solution. The slurry was partially concentrated in vacuo. After stirring for 1 h at room temperature, the solid was collected by vacuum filtration, washed with distilled H$_2$O until the pH of the filtrate was 4.0 and with hexane. Drying in vacuo yielded 5.85 g (64%) of title benzaldehyde as an off-white solid-Chiral HPLC indicated 99.7:0.3 ratio of title aldehyde to its enantiomer (99.4% ee)

EXAMPLE 3

[2S-(2α, 3aα, 4β, 7β, 7aα)]-2-(Octahydro-3-oxo-4,7-epoxy-isobenzofuran-1-yl)benzaldehyde A. (2S, 4S, 5S)-2-(2-Bromophenyl)-3,4-dimethyl-5-phenyloxazolidine Following the procedure of Example 1, Part B except substituting (+)-pseudoephedrine for (−)-pseudoephedrine, the title compound was obtained.

B. (2S,4S,5S)-2-(3,4-Dimethyl-5-phenyloxazolidin-2-yl)phenyl lithium

Under an argon atmosphere, 2.5M n-BuLi (750 uL, 1.88 mmol) was added to a solution of Part A oxazolidine (594 mg, 1.79 mmol) in distilled THF (5 mL) at −77° C. (internal) to form title lithiated compound.

C. [1R-[1α,2α,3α[2R-(2α,3β,4α,5β)],4α]]-3-[2-(3,4-Dimethyl-5-phenyl-2-oxazolidinyl)-benzoyl]-7-oxabicyclo[2.2.1]heptane-2-carboxylic acid, lithium salt After stirring at −78° C. for 2 h the Part B lithiated oxazolidine was added dropwise to a solution of (3aα,4β,7β,7aα)hexahydro-4,7-epoxy-isobenzofuran-1,3-dione (300 mg, 1.78 mmol, 1.0 eq) in THF (5 mL) at −78° C. The internal temperature rose as high as −65° C. during the addition. The resulting yellow mixture was stirred for 2 h at −78° C. and then quenched with 15 mL of anhydrous MeOH to give title compound.

D. [2S-(2α,3aα,4β,7β,7aα)]-2-(Octahydro-3-oxo-4,7-eopxyisobenzofuran-1-yl)benzaldehyde The reaction temperature of the Part C reaction mixture was lowered to −77° C. and MgBr$_2$·Et$_2$O (951 mg, 3.68 mmol, 2.1 eq) was added followed by NaBH$_4$ (127 mg, 3.35 mmol, 1.9 eq). The mixture was allowed to warm to −30° C. and stirring was continued for 1.2 h. The reaction was quenched with acetone (5 mL) and poured into ice-cold 10% HCl (15 mL). After stirring at room temperature for 15 h, the reaction was concentrated in vacuo and poured into a separatory funnel containing 15 mL of 10% HCl. After extracting 2× with EtOAc (50 mL+25 mL), the organic layer was collected, washed with brine, dried over MgSO$_4$ and concentrated to yield 353 mg (76%) of a tan solid. Column chromatography (silica gel, 2:1 hexane/EtOAc followed by 1:1 hexane/EtOAc) yielded 238 mg (51%) of title aldehyde as a white solid, Chiral HPLC indicated a 65:35 ratio of title aldehyde to its enantiomer (30% e.e.).

EXAMPLE 4

[2S-(2α, 3aα,4β,7β,7aα]-2-(Octahydro-3-oxo-4,7-epoxy-isobenzofuran-1-yl)benzaldehyde Following the procedure of Example 1 except substituting (+)-ephedrine for (−)-pseudoephedrine, the title compound is obtained (65% ee).

EXAMPLE 5

[2S-(2α, 3aα,4β,7β,7aα]-2-(Octahydro-3-oxo-4,7-epoxy-isobenzofuran-1-yl)benzaldehyde Following the procedure of Example 2 except substituting (−)-ephedrine for (+)-pseudoephedrine, the title compound is obtained (26% ee).

EXAMPLE 6

[1S-(1α,2α,3α,4α)]-2-[[2-(3-Methoxy-3-oxopropyl)-Phenyl]methyl]-7-oxabicyclo[2.2.1]heptane-3-carboxylic acid (via Scheme III)

A. [1S-[1α(E),3aα,4β,7β,7aα]]-3-[2-Octahydro-3-oxo-4,7-epoxyisobenzofuran-1-yl)phenyl]-2-propenoic acid, methyl ester In a 250 mL flask was placed Example 1 benzaldehyde (obtained from two different batches) (9.44 g, 36.54 mmole), lithium chloride (1.7 g, 40.19 mmole) and acetonitrile (145 mL). The solution was stirred magnetically under an argon atmosphere. Trimethylphosphonoacetate (7.32 g, 40.19 mmole) was added via syringe followed by 1,8-diazabicyclo[5.4.0]undec-7-ene (DBU) (6.01 mL, 40.19 mmole). The solution became cloudy and the temperature of the reaction rose to 42° C. After 75 minutes, TLC indicated the reaction to be complete. The mixture was poured into aqueous saturated sodium bicarbonate (500 mL) and extracted with methylene chloride (2×500 mL). The combined organic layers were dried over anhydrous magnesium sulfate, filtered, concentrated on a rotary evaporator (bath temp. 35° C., ~80 mm Hg) and dried under high vacuum (~0.5 mm Hg) at room temperature to provide 11.36 g (98.9% yield) of crude title compound as a yellow, crystalline solid.

B. [1S-(1α, 2α, 3α, 4α)]-2-[[2-(3-Methoxy-3-oxopropyl)phenyl]methyl]-7-oxabicyclo[2.2.1]-heptane-3-carboxylic acid The Part A crude vinyl ester (11.36 g) was placed in a 250 mL flask and dissolved in THF (35 mL) and methanol (70 mL). To the magnetically stirred solution was added Pearlman's catalyst (Aldrich) (Pd(OH)$_2$/C) (1.14 g). The flask was evacuated, then connected to a balloon filled with hydrogen. After being stirred at room temperature for 2 hours, a second portion of Pearlman's catalyst (1.14 g) was added. The flask was re-evacuated and reconnected to the balloon filled with hydrogen. The mixture was stirred at room temperature for an additional 2 hours. TLC indicated complete conversion to title compound. The balloon was removed and celite (2.0 g) was added to the mixture and stirred for 10 minutes. The mixture was filtered through a pad of celite (45×25 mm). The pad was washed with methanol (50 mL). The filtrate was concentrated on a rotary evaporator as described above to provide a yellow oil. The oil was dissolved in methylene chloride (100 mL) and dried over anhydrous magnesium sulfate. The solution was filtered, concentrated on a rotary evaporator as described above, and dried under high vacuum (~0.5 mm Hg) to provide 11.81 g (101.6% yield) of crude title compound.

The above crude title compound (11.81 g) was dissolved in hot ethyl acetate (23 mL) and diluted with hot heptane (46 mL). The mixture was allowed to cool while being stirred magnetically. The mixture was seeded at a temperature of 58° C. with crystals of title compound. Upon cooling to room temperature, a significant quantity of title compound had crystallized from the solution. An additional portion of heptane (65 mL) was added and the mixture was stirred for 5 minutes. The mixture was allowed to stand at room temperature overnight. The resulting solid was collected by suction filtration, washed with heptane (50 mL), then dried under high vacuum at room temperature to provide 7.32 g (62.9% yield) of title compound containing small traces of yellow material.

The solid and the mother liquor were recombined and dissolved in ethyl acetate (120 mL) and treated with Darco KB activated carbon (1.2 g). The mixture was heated to reflux for 2 minutes, then allowed to cool to room temperature. Celite (2.4 g) was added, and the mixture was stirred for 10 minutes, then filtered through a pad of celite (45×25 mm). The pad was washed with ethyl acetate (50 mL). The flitrates were concentrated on a rotary evaporator as described above to provide a pale yellow oil. The oil was dissolved in ethyl acetate (23 mL), heated to reflux and diluted with heptane (46 mL). The mixture was then allowed to cool to room temperature with stirring. The mixture was seeded with crystals of title compound. After stirring at room temperature for ~15 minutes, additional heptane (65 mL) was added. The flask was placed in a cold room (~4° C.) overnight. The resulting crystals were collected by suction filtration, washed with heptane (50 mL) and dried under high vacuum (~0.5 mm Hg) at room temperature to provide 9.97 g (85.7% yield) of title compound.

EXAMPLE 7

[1S-(1α,2α,3α,4α)]-2-[[2-(3-Methoxy-3-oxopropyl)-phenyl]methyl]-7-oxabicyclo[2.2.1]heptane-3carboxylic acid (via Scheme IV)

A. [1S-[1α(E),3aα,4β,7β,7aα]]-3-[2-(Octahydro-3-oxo-4,7-epoxyisobenzofuran-1-yl)-phenyl]-2-propenoic acid A dry, argon purged 250 mL one-necked flask was charged with Example 2 aldehyde (10 g, 38.8 mmole), malonic acid (18.1 g, 174 mmole) and pyridine (20 mL). The flask was equipped with a reflux condenser and the mixture was heated at 85° C. in an oil bath. The solids dissolved after heating for ten minutes. Piperidine (0.380 mL) was added. The reaction was stirred at 85° C. for 18 hours and cooled to room temperature. 10% HCl (200 mL) was added over 15 minutes. The solution became thick with the formation of a precipitate. The slurry was stirred at room temperature for three hours. The solid was collected in a medium scintered glass funnel and washed with water (3×30 mL). A clean 500 mL receiving flask was attached to the funnel. Acetone (~240 mL) was added to dissolve the solid and was then pulled through the funnel. The filtrate was concentrated on a rotary evaporator to provide 10.8 g (93%) of crude title acid as a white solid which was used in the next step without any additional purification.

B. [1S-[1α(E),3aα,4β,7β,7aα]]-3-[2-(Octahydro-3-oxo-4,7-epoxyisobenzofuran-1-yl)-phenyl]-2-propenoic acid, methyl ester The above crude Part A acid (10.7 g, 35.7 mmole) was mixed with methanol/sulfuric acid (360 mL) at room temperature under argon in a 500 mL 2-necked flask equipped with a reflux condenser. The mixture was heated to 50° C. in an oil bath. As it warmed, the solids dissolved. After six hours, the solution was cooled to room temperature and concentrated on a rotary evaporator to a slurry (~50 mL). The slurry was diluted with ethyl acetate (100 mL). The solution was washed with aqueous saturated sodium bicarbonate (3×25 mL) and aqueous saturated NaCl (1×25 mL). The organic layer was dried over magnesium sulfate, filtered and concentrated on a rotary evaporator to provide 10.6 g (95%) of crude title ester as an off-white hard solid which was used in the next step without any additional purification.

C. [1S-(1α,2α,3α,4α)]-2-[[2-(3-methoxy-3-oxopropyl)phenyl]methyl]-7-oxabicyclo[2.2.1]-heptane-3-carboxylic acid The above crude Part B ester (10.3 g, 32.8 mmole) was dissolved in a solution of THF (40 mL) and methanol (80 mL) in a 250 mL one-necked flask equipped with a three-way valve. The valve was connected to a balloon of hydrogen and the house vacuum. The flask was evacuated and filled with hydrogen three times by turning the valve. Pearlman's catalyst (1.03 g, 10% by weight) was added. The flask was again evacuated and filled with hydrogen three times. The reaction was stirred at room temperature for two hours.

Celite (15 g) was added to the flask and stirred 10 minutes. The mixture was filtered through a pad of celite and concentrated on a rotary evaporator. The residue had a grey color. It was dissolved in methylene chloride (50 mL), dried over magnesium sulfate and filtered through another pad of celite. The filtrate was concentrated on a rotary evaporator. The product was again dissolved in methylene chloride (25 mL) and filtered through a thick pad of celite to provide a clear, yellow solution. The solvent was removed on a rotary evaporator to provide 10.4 g (99%) of crude title acid as a mixture of a white solid, a colorless oil and a dark yellow oil.

The crude product was dissolved in boiling ethyl acetate (25 mL). While boiling, heptane (50 mL) was added slowly to maintain reflux. The clear, pale yellow solution was then allowed to cool to room temperature with stirring. The mixture was seeded with crystals of title acid when it reached 50° C., and again when it reached 45° C. The mixture became cloudy and then thick with solids. After the mixture had reached room temperature (~28° C.), additional heptane (70 mL) was added. The flask was placed in a cold room (~4° C.) over the weekend. The resulting crystals were collected by suction filtration, washed with heptane (3×50 mL) and dried under house vacuum at room temperature for 24 hours to provide 9.22 g (88%) of title acid as a fluffy white solid. The overall yield from Example 2 aldehyde was 77.8%.

EXAMPLE 8

N-Pentyl-L-Serinamide

A. Carbobenzyloxy-L-serine

L-Serine (20.00 g, 190.3 mmol) was dissolved in water, and aqueous sodium hydroxide was added to adjust the pH of the solution to about 8.5 while maintaining the temperature at about 25° C. Benzyl chloroformate (36.0 g, 211.0 mmol) was added while maintaining the pH between 8.3 and 8.5 by the addition of aqueous sodium hydroxide and the temperature was maintained at about 30° C. The mixture was stirred for about 2 hours. The reaction mixture was extracted with methylene chloride. The phases were separated, and the pH of the aqueous phase was adjusted to about 7 with concentrated hydrochloric acid. The aqueous phase was heated to about 40° C. under low vacuum to remove any residual methylene chloride. Water was added and the aqueous solution was heated to about 60° C. The pH was adjusted to about 2 with concentrated hydrochloric acid while maintaining the temperature at about 60° C. The solution was cooled to about 50° C. while stirring and seed crystals were added with stirring, cooling was continued to about 0° C. to complete the crystallization.

The product was collected and the cake was washed with cold (about 5° C.) water. The product was dried under vacuum at about 40° C. to afford carbobenzyloxy-L-serine.

B. N-Pentyl-L-serinamide, oxalate (1:1) salt

Under an inert atmosphere, 1,8-diazabicyclo[5.4.0]undec-7-ene (5.10 g, 33.5 mmol) was added to a suspension of Part A carbobenzyloxy-L-serine (7.50 g, 31.4 mmol) in ethanol. Ethyl acetate was added and the mixture was agitated (optionally, with heating up to about 50° C.) to obtain a clear solution. Pyridine (0.25 g, 3.2 mmol) was added and the mixture was cooled to about −30° C. Trimethylacetyl chloride (4.12 g, 34.2 mmol) was added and the mixture was maintained at about −30° C. With cooling, n-amylamine (3.00 g, 34.4 mmol) was added and the mixture was stirred at about −10° C. for about 2 hours. Cooling was discontinued and aqueous phosphoric acid was added. The mixture was warmed to about 10° C. and the phases were separated. The organic solution was washed sequentially with aqueous phosphoric acid, aqueous potassium carbonate, and brine. Throughout these extractions, the aqueous phase was back extracted with ethyl acetate. The combined organic solution was distilled under vacuum at about 25° C. while ethanol was added until all of the ethyl acetate was removed. Under an inert atmosphere, 10% palladium on carbon (50% water, 0.75 g) was added. The resulting mixture was purged with nitrogen and then stirred in the presence of hydrogen at about 25° C. for about 6 hours. The catalyst was removed by filtration, and the clear filtrate was partially concentrated under vacuum at about 30° C. The concentrated filtrate was added to a solution of oxalic acid dihydrate (4.35 g, 34.5 mmol) in ethanol and water and a thick precipitate was formed. The suspension was heated to reflux to obtain a clear solution. Water was added at the reflux temperature until a slight turbidity was observed. The mixture was cooled to about 0° C. and stirred until crystallization was complete (about 1 hour). The product was collected and the cake was washed with ethanol. The product was dried under vacuum at about 25° C. to afford title compound.

EXAMPLE 9

1S-(1α,2α,3α,4α)]-2-[[3-[4-[(Pentylamino)carbonyl]-2-oxazolyl]-7-oxabicyclo[2.2.1]hept-2-yl]methyl]benzenepropanoic acid, monosodium salt A. [1S-[1α,2α,3α(R*),4α]]-2-[[3-[[[1-(Hydroxymethyl)-2-oxo-2-(pentylamino) ethyl]amino]carbonyl]-7-oxabicyclo[2.2.1]hept-2-yl]methyl]benzenepropanoic acid, methyl ester Under an inert atmosphere, a catalytic amount of dimethylformamide (0.067 mL, 0.87 mmol) was added to a solution of Example 7 carboxylic acid (6.66 g, 20.9 mmol) in toluene and the resulting mixture was cooled to about 0° C. while maintaining the temperature below 0° C., oxalyl chloride (2.96 g, 23.3 mmol) was added and the mixture was stirred at about 5° C. for about 3 hours. The resulting acid chloride solution was partially concentrated under vacuum at about 40° C. and then used in the coupling reaction described below.

Meanwhile, Example 8 amide (6.17 g, 23.3 mmol) was added to a solution of sodium bicarbonate (9.63 g, 115 mmol) in water while the temperature was maintained at about 20° C. Methyl ethyl ketone was added and the biphasic mixture was cooled to about 0° C. While maintaining the temperature at about 0° C., the previously prepared acid chloride solution was added with stirring. The mixture was stirred at about 5° C. for about 20 hours and then heated to about 60° C. and the phases were allowed to separate. The organic phase was washed at about 50° C. sequentially with saturated sodium bicarbonate solution, aqueous phosphoric acid, and brine. The organic solution was partially concentrated under vacuum at about 40° C. to obtain a thick suspension. n-Heptane was added and the resulting mixture was cooled to about 20° C. with stirring. The product was collected and the cake was washed with n-heptane. The product was dried under vacuum at about 35° C. to afford title ester.

B.  [1S-[1α,2α,3α(R*),4α]]-2-[[3-[4,5-Dihydro-4-[(Pentylamino)carbonyl]-2-oxazolyl]7-oxabicyclo[2.2.1]hept-2-yl]methyl]benzene-propenoic acid, methyl ester Under an inert atmosphere, Part A ester (7.00 g, 14.7 mmol) was dissolved in dry dimethylformamide. The moisture content of the resulting solution must be <0.1% w/w; if it was higher, the solution was first dried by vacuum distillation of a portion of the solvent and dry dimethylformamide was added to restore the original solution volume. Triethylamine (4.29 g, 42.4 mmol, plus approximately 1 mmol per mmol of water measured in the Part A ester solution) was added and the mixture was cooled to about 0° C. While maintaining the temperature below 5° C., methanesulfonyl chloride (2.02 g, 17.6 mmol, plus approximately 0.4 mmol per mmol of water measured in the Part A ester solution) was added. The reaction mixture was stirred at about 5° C. for about 5 hours. The mixture was warmed to about 25° C. and stirred for about 20 hours. Cold (about 5° C.) water was added while maintaining the pH at about 8.0 by the addition of aqueous phosphoric acid. The resulting suspension was stirred at about 10° C. for about 1 hour. The product was collected and the cake was washed with cold (about 5° C.) water. The product was dried under vacuum at about 25° C. to afford title compound.

C.  [1S-(1α,2α,3,4α)]-2-[[3-[4-[(Pentylamino)-carbonyl]-2-oxazolyl]-7-oxabicyclo[2.2.1]hept-2-yl]methyl]benzenepropanoic acid, methyl ester Under an inert atmosphere, hexamethylene-tetramine (5.89 g, 42.0 mmol) was added to a mixture of copper-(II) bromide (8.63 g, 38.6 mmol) and methylene chloride. A solution of 1,8-diazabicyclo[5.4.0]undec-7-ene (6.38 g, 41.9 mmol) in methylene chloride was added with slight cooling to maintain the temperature at about 30° C. A solution of Part B ester (4.50 g, 9.86 mmol) in methylene chloride was added, and the reaction mixture was stirred at about 30° C. for about 14 hours. If necessary, additional copper(II) bromide was added to complete the reaction. The mixture was cooled to about 20° C. and filtered, and the cake was washed with methylene chloride. At this point, the filtrate may be combined with the filtrate from another run. The filtrate was concentrated under vacuum at about 30° C., and ethyl acetate, water and aqueous ammonia were added to the resulting residue. The phases were separated, and the organic phase was washed with a mixture of water and aqueous ammonia. The resulting aqueous solution was back extracted with ethyl acetate. The combined organic phase was washed sequentially with aqueous phosphoric acid and brine. Brine was added to the organic phase and the pH was adjusted to about 7 with saturated sodium bicarbonate. The organic solution was separated and partially concentrated under vacuum at about 40° C. Seed crystals of title compound were added followed by n-heptane. The remaining ethyl acetate was replaced with n-heptane by a vacuum-distillation exchange procedure at a temperature of 40° C. or below. The product was collected and the cake was washed with n-heptane. The product was dried under vacuum at about 25° C. to afford title compound.

D.  [1S-(1α, 2α, 3α, 4α)]-2-[[3-[4-[(Pentylamino) carbonyl]-2-oxazolyl]-7-oxabicyclo-[2.2.1]hept-2-yl]methyl]benzenepropanoic acid. monosodium salt Under an inert atmosphere, 1N sodium hydroxide (3.6 mL, 3.6 mmol) was added to a cold (about 5° C.) solution of Part C ester (0.600 g, 1.32 mmol) in tetrahydrofuran. The reaction mixture was stirred at about 25° C. for about 4 hours. The reaction mixture was partially concentrated under vacuum at about 35° C. The concentrated solution was diluted with water and then washed with diethyl ether. The phases were separated and the pH of the aqueous solution was adjusted to about 7 with concentrated hydrochloric acid. Methylene chloride was added and acidification was continued with stirring to a pH of about 2. The phases were separated and the aqueous layer was extracted with methylene chloride. The resulting combined organic extract was washed sequentially with water and brine. The organic solution was dried over anhydrous magnesium sulfate, filtered and concentrated under vacuum at about 25° C. to a solid. The resulting solid was dissolved in hot (about 90° C.) acetonitrile, and the solution was allowed to stand at room temperature without stirring for about 12 hours. The product was collected and the cake was washed with cold (about 5° C.) acetonitrile. The product was dried under vacuum at about 35° C. to afford title compound.

Under an inert atmosphere, title compound (461 g, 1.04 mol) was dissolved in acetone at about 50° C. The resulting solution was cooled to about 35° C. and a solution of 25% w/w sodium methoxide in methanol (0.264 mL, 1.15 mol) was added. The resultant slurry was allowed to cool to about 25° C. with stirring. The product was collected and the cake was washed with acetone. The product was dried under vacuum at about 35° C. to afford title compound.

EXAMPLES 10 TO 13

[2S- (2α, 3aα, 4β, 7β, 7aα]-2-(Octohydro-3-oxo-4,7-epoxyisobenzofuran-1-yl)benzaldehyde Following the procedure of Example 2 except substituting the following oxazolidines for the Example 1 phenyloxazolidine, the title benzaldehyde compound is prepared:

10. (2R, 4R) -2- (2-Bromophenyl) -3-methyl-4-phenyl-1,3 -oxazolidine.
11. (2R, 4R) -2- (2-Bromophenyl) -3-isopropyl-4-phenyl-1,3-oxazolidine.
12. (2R,4R)-2-(2-Bromophenyl)-4-isopropyl-3-methyl-1,3-oxazolidine.
13. (2R,4R)-2-(2-Bromophenyl)-4,3-diisopropyl-1,3-oxazolidine.

The above oxazolidines and/or their preparation are described by Takahashi et al, Synthesis, July 1993, pp 681–683.

What is claimed is:

1. A method for preparing an intermediate having the structure as defined in claim 1, which comprises reacting an oxazolidine of the structure

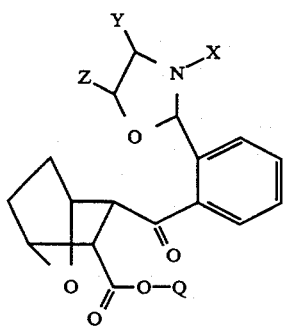

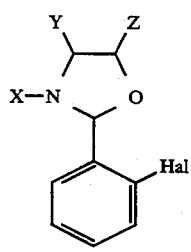

with an alkylated lithium compound to form a lithiated oxazolidine of the structure

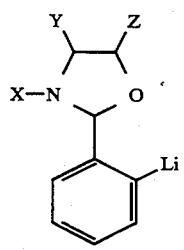

and reacting the lithiated oxazolidine or the corresponding Grignard reagent

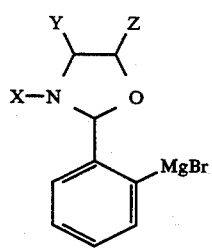

with an anhydride of the structure

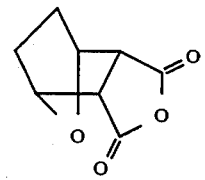

to form the desired intermediate product.

2. The method as defined in claim 1 wherein Y is $CH_3$, Z is $C_6H_5$ and X is $CH_3$.

3. The method as defined in claim 1 wherein the starting oxazolidine has the structure

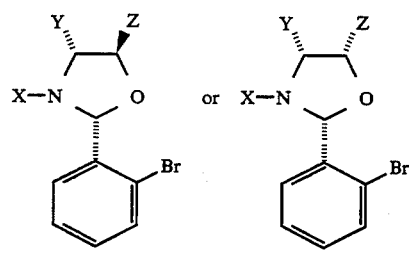

which is reacted with an alkylated lithium to form the corresponding tithiated oxazolidine which is reacted with $MgBr_2$ to form the corresponding Grignard reagent

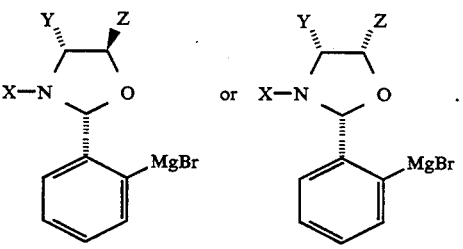

4. The method as defined in claim 1 wherein X is $CH_2$, Y is $CH_3$ and Z is $C_6H_5$.

5. The method as defined in claim 1 wherein the lithiated oxazolidine has the structure

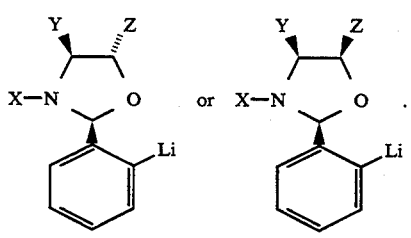

6. The method as defined in claim 1 wherein X is $CH_3$, Y is $CH_3$ and Z is $C_6H_5$.

* * * * *